United States Patent [19]
Luong et al.

[11] Patent Number: 5,432,274
[45] Date of Patent: Jul. 11, 1995

[54] REDOX DYE AND METHOD OF PREPARATION THEREOF USING 2-HYDROXYPROPYL-β-CYCLODEXTRIN AND 1,1'-DIMETHYLFERROCENE

[75] Inventors: John H. T. Luong, Mount Royal; Keith B. Male, Pierrfonds; Shishan Zhao; R. Stephen Brown, both of Montreal, all of Canada

[73] Assignee: National Research Council of Canada, Ottawa, Canada

[21] Appl. No.: 97,901

[22] Filed: Jul. 28, 1993

[51] Int. Cl.⁶ .................. C08B 37/16; C07F 17/02; C12P 19/04; C12N 11/14
[52] U.S. Cl. .................. 536/103; 536/124; 556/143; 435/41; 435/72; 435/101; 435/176; 435/177
[58] Field of Search ............ 536/103, 124; 556/143; 435/41, 72, 101, 189, 176, 177

[56] References Cited
U.S. PATENT DOCUMENTS

| | | | |
|---|---|---|---|
| 5,116,730 | 5/1992 | Artiss et al. | 435/15 |
| 5,200,181 | 4/1993 | Soltys et al. | 424/94.3 |

OTHER PUBLICATIONS

Luong et al, Anal. Biochem. 212 (1): 269–276 (1993).
Harada et al, J. Chem. Soc. Dalton Trans., pp. 729–732 (1988).
Strelets et al, J. Electroanal Chem 310:179–186 (1991).
Ryabov et al, Bioelectrochem. Bioenerg. 24(2): 257–262 (1990).
Aldrich Catalogue, pp. 501, 714–715 (1992).
Sigma Catalogue, p. 459, (1992).

*Primary Examiner*—Marian C. Knode
*Assistant Examiner*—Francisco C. Prats
*Attorney, Agent, or Firm*—Juliusz Szereszewski

[57] ABSTRACT

Ferricinium or ferricinium-based compounds are useful as blue redox dyes suitable for monitoring various enzymatic oxidation processes. A process for preparing such dyes is proposed which involves complexing ferrocene or its derivative with a cyclodextrin. The resulting yellow inclusion complex, an intermediate of the redox dye, is then oxidized electrochemically or by a reaction with bilirubin oxidase to form blue redox dyes which exhibit absorption peaks at 620 or 650 nm. Both the reduced form and the oxidized form of the dye are water-soluble.

8 Claims, 10 Drawing Sheets

REDOX DYE AND METHOD OF PREPARATION THEREOF USING 2-HYDROXYPROPYL-β-CYCLODEXTRIN AND 1,1'-DIMETHYLFERROCENE

FIELD OF THE INVENTION

This invention relates to ferricinium-based water-soluble blue dyes useful for, e.g., the spectrophotometric determination of certain enzymatic oxidation reactions, and particularly to processes for the preparation of the dyes and their intermediates.

BACKGROUND OF THE INVENTION

Oxidase systems have been exploited for determination of various substrates for many years. For example, in the presence of oxygen the enzyme glucose oxidase catalyzes the oxidation of glucose by oxygen to gluconolactone (gluconic acid) and hydrogen peroxide; lactate is oxidized by lactate oxidase; glutamic acid is oxidized by glutamate oxidase, etc; hydrogen peroxide being the by-product of all these reactions.

The concentration of the substrate, e.g. glucose, can be followed by monitoring the concentration of $H_2O_2$. For example, addition of enzyme peroxidase and a chromogenic oxygen acceptor, such as colorless o-dianisidine, results in the reaction of hydrogen peroxide and o-dianisidine with formation of a measurable color (oxidized o-dianisidine, brown, absorption at 500 nm). The method is not widely used because O-dianisidine is toxic. In any case, this approach requires more than one enzyme (oxidase and peroxidase). Alternatively, $H_2O_2$ can be monitored by NADH peroxidase and the expensive cofactor, NADH (a reduced form of nicotinamide adenine dinucleotide).

It is desirable to eliminate the use of peroxidase. Also, the spectrophotometric determination of glucose in some body fluids or solutions with pronounced color faces serious difficulty because of color masking. Blue dyes are advantageous in this regard because their absorption peaks are distant from the bands characteristic of most biological fluids.

Water-insoluble ferrocene [bis($\eta^5$-cyclopentadienyl)iron] and its derivatives have been studied by Cass, A. E. G. et al, Anal. Chem. 56, 667–671 (1984) and by Hill, H. A. O. et al, Biosensors, a Practical Approach (Cass, A. E. G., Ed.), pp. 19–46, IRL Press, Oxford (1990) to develop mediated amperometric biosensors because of their electron-exchange properties with various enzymes. To replace oxygen as an electron receptor, ferrocene must be first oxidized at a platinum or carbon electrode surface to ferricinium through the loss of one electron from the metal atom.

The ferricinium cation is water-soluble and able to react with several reduced oxidoreductases as follows:

Substrate + Enzyme$_{ox}$ → Enzyme$_{red}$ + Product    (1)

2 Ferricinium + Enzyme$_{red}$ → 2 Ferrocene + Enzyme$_{ox}$ + 2H$^+$    (2)

The redox couple—ferrocene and ferricinium—exhibits a marked difference in UV-VIS absorption spectra. Ferrocene in 95% ethanol is yellow and features two wavelength bands at 325 and 440 nm. Ferricinium solutions exhibit a characteristic dichroism with an absorption peak at 620 nm, i.e. dilute solutions appear blue or green, while more concentrated solutions are blood red. Apparently, ferricinium or its derivatives could be used in spectrophotometric assays involving oxidoreductases if they can be prepared from water-soluble forms of ferrocenerelated compounds. However, ferrocene and its derivatives (except for carboxyl ferrocene) are virtually waterinsoluble.

SUMMARY OF THE INVENTION

It is an object of the invention to provide a water-soluble redox dye useful for the monitoring of enzymatic oxidation reactions.

It is another object of the invention to provide a water-soluble form of ferrocene or ferrocene-related compounds to enable the use of the ferrocene-ferricinium redox couple to monitor enzymatic oxidation and some other redox reactions.

It has been found that the problem of solubility of ferrocene or its derivatives can be overcome by complexing these compounds with certain cyclodextrins. The resulting water-soluble inclusion complexes are convenient intermediates of ferricinium based blue dyes.

According to one aspect of the invention, there is provided a process for preparing a water-soluble intermediate of a redox dye, the process comprising reacting ferrocene or its suitable derivative with a water-soluble cyclodextrin selected from α, β, γ, and 2-hydroxypropyl-β-cyclodextrin, (hp-β-CD) to obtain a water-soluble inclusion complex. Preferably, the ferrocene derivative is 1,1'-dimethylferrocene.

The intermediate can be oxidized to form a water-soluble redox dye whereby the ferrocene or ferrocene-derivative undergoes oxidation to its respective ferricinium form and a blue redox dye results. The oxidation can be carried out by electrochemical means or by reacting the inclusion complex with the enzyme bilirubin oxidase.

According to another aspect of the invention, there is provided a ferrocene-based soluble inclusion complex comprising a cyclodextrin and ferrocene or a suitable ferrocene derivative complexed therewith, the cyclodextrin being selected from the group consisting of α-cyclodextrin, β-cyclodextrin, γ-cyclodextrin and 2-hydroxypropyl-β-cyclodextrin.

The suitability of the ferrocene derivative is determined by the size of the particle to match the size of the cavity of the cyclodextrin particle, and by the electrochemical potential E° of the derivative.

Through oxidation of the inclusion complex, water-soluble redox dyes are provided which exhibit absorption peaks at 620 or 650 nm for ferricinium and dimethylferricinium, respectively.

The redox dyes of the invention are useful for monitoring the activity of various oxidases and the concentration of enzymatically oxidizable substrates.

BRIEF DESCRIPTION OF THE DRAWINGS

The invention will be described hereinbelow in conjunction with drawings, in which

FIG. 2A dotted line denotes FeCp$_2$, 4 mM; solid line denotes FeCp$_2$+, 2.2 mM;

FIG. 2B: dotted line denotes DMFeCp$_2$, 4.5 mM; solid line denotes DMFeCp$_2$+, 3.4 mM;

Figure 4:
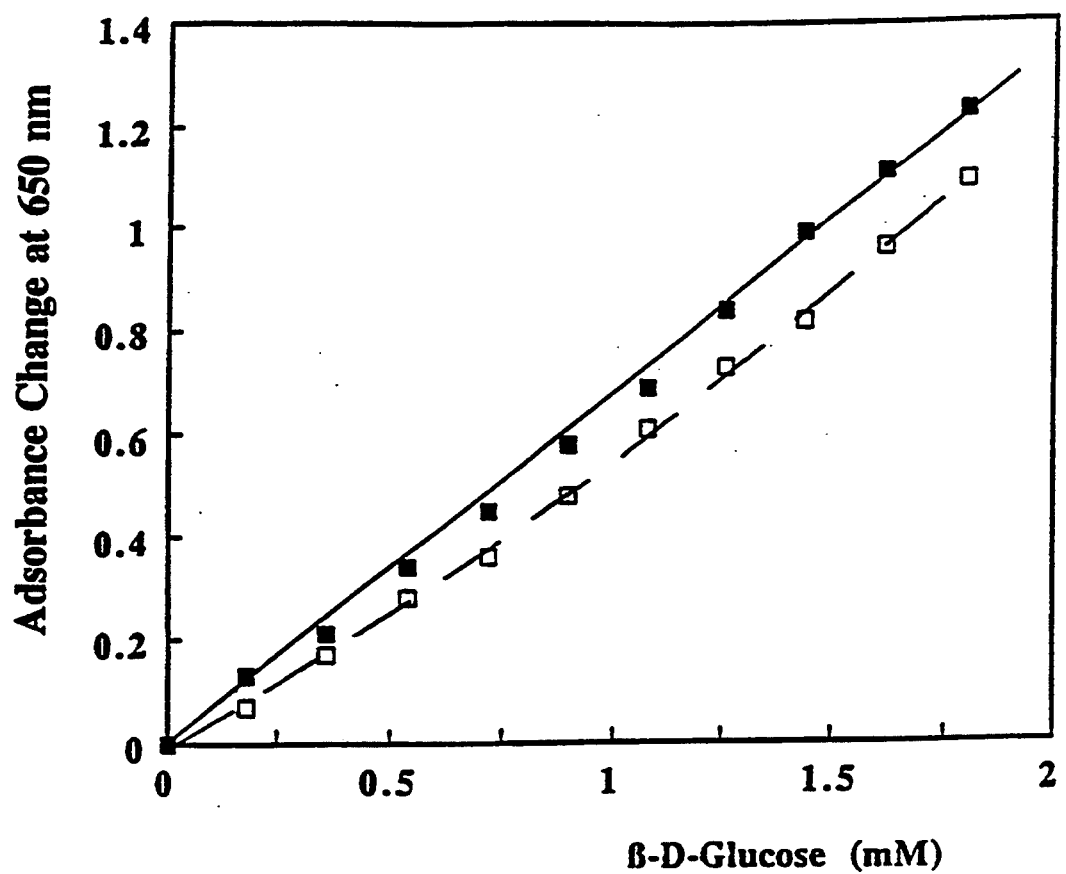

○—ascorbic acid (pH 5.2, acetate 20 mM; slope=0.649±0.003; R$^2$=0.999;

■—uric acid (pH 7.8, phosphate 150 mM); slope=0.654±0.004; R$^2$=0.999;

□—sulfite (pH 9.0, borate 25 mM); slope=0.657 ±0.010; R$^2$=0.999;

FIG. 4 illustrates the reduction of DMFeCp$_2$+ by β-D-glucose in the presence of glucose oxidase with and without oxygen removal using 20 mM acetate buffer pH 5.2 (slope is determined at 95% confidence interval);

□—oxygen present

Figure 5:
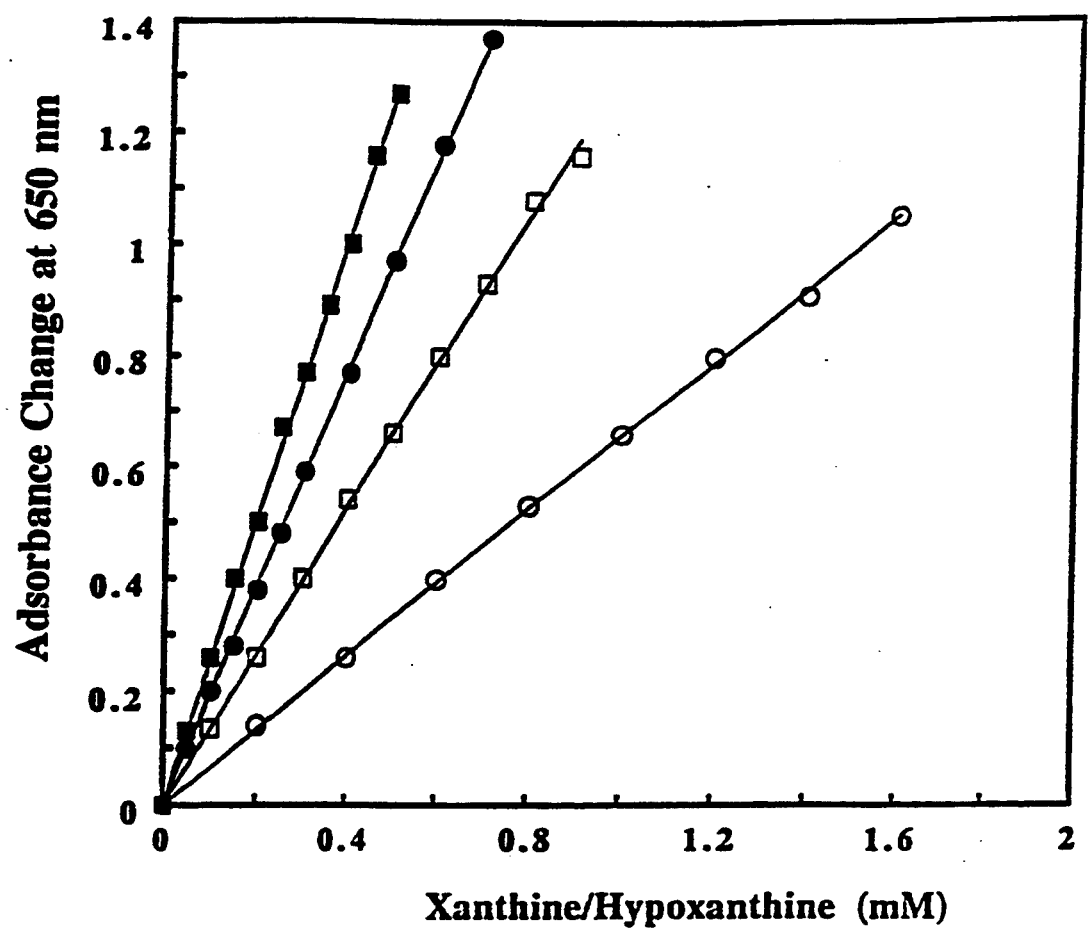

■—oxygen removed by 0.4 mM Na$_2$SO$_3$ or nitrogen bubbling; slope=0.671±0.011; R$^2$=0.999;

FIG. 5 illustrates reduction of DMFeCp$_2$+ by hypoxanthine/xanthine in the presence of xanthine oxidase at different pH conditions (slope is determined at 95% confidence interval)

Figure 6:
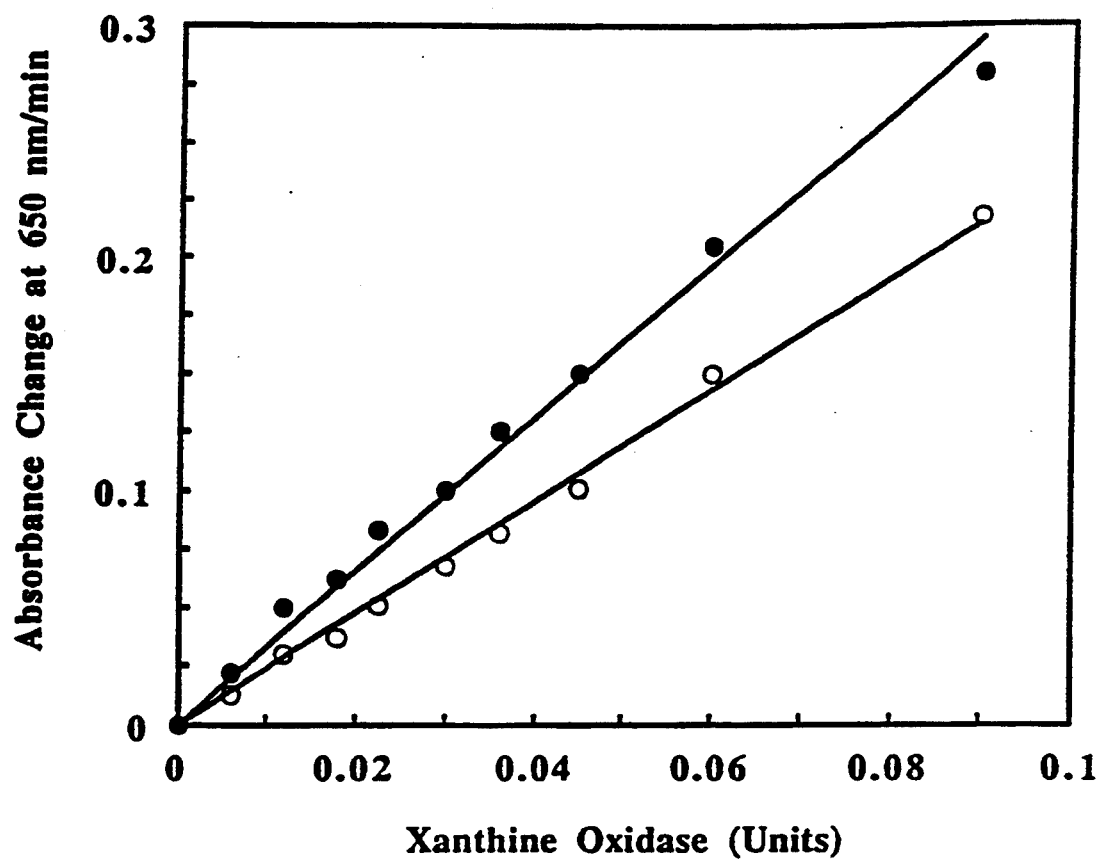

○—xanthine, pH 5.2, acetate 20 mM; slope=0.658±0.004; R$^2$±0.999;

□—hypoxanthine, pH 5.2, acetate 20 mM; slope=1.323±0.006; R$^2$=0.999;

●—xanthine, pH 9.0, borate 25 mM; slope=1.950±0.003; R$^2$=0.999;

■—hypoxanthine, pH 9.0, borate 25 mM; slope=2.555±0.005; R$^2$=0.999;

FIG. 6 illustrates the rate of reduction of DMFeCp$_2$+ by xanthine oxidase at pH 9.0 (slope is determined at 95% confidence interval);

○—xanthine (2.39 OD$_{650}$ nm/unit); slope=2.39±0.10; R$^2$=0.999;

●—hypoxanthine (3.28 OD$_{650}$ nm/unit); slope=3.28±0.10; R$^2$=0.999.

Figure 7:
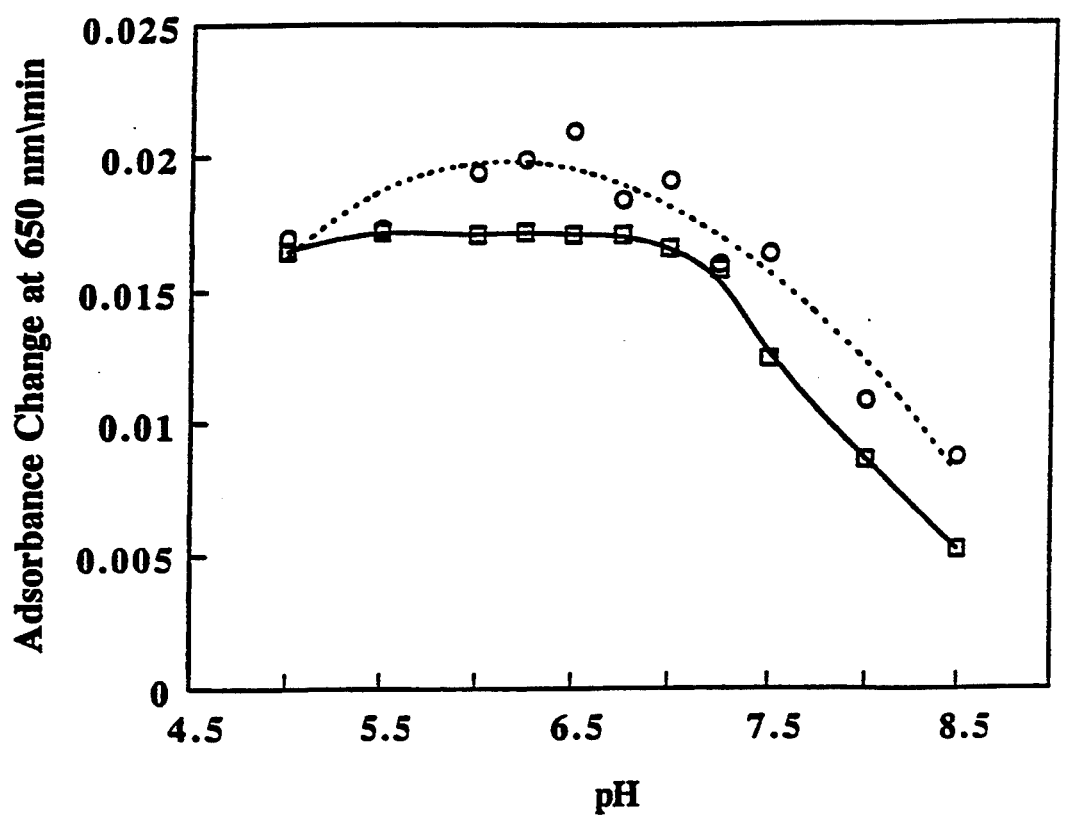

FIG. 7 is a graph illustrating the activity vs pH profile of soluble bilirubin oxidase (0.005 IU) for the oxidation of 1,1'-dimethylferrocene (DMCFeCp$_2$) to 1,1'-dimethylferricinium (DMFeCp$_2$+):

□—0.75 mM DMFeCp$_2$;

○—7.5 mM DMFeCp$_2$+.

Figure 8:
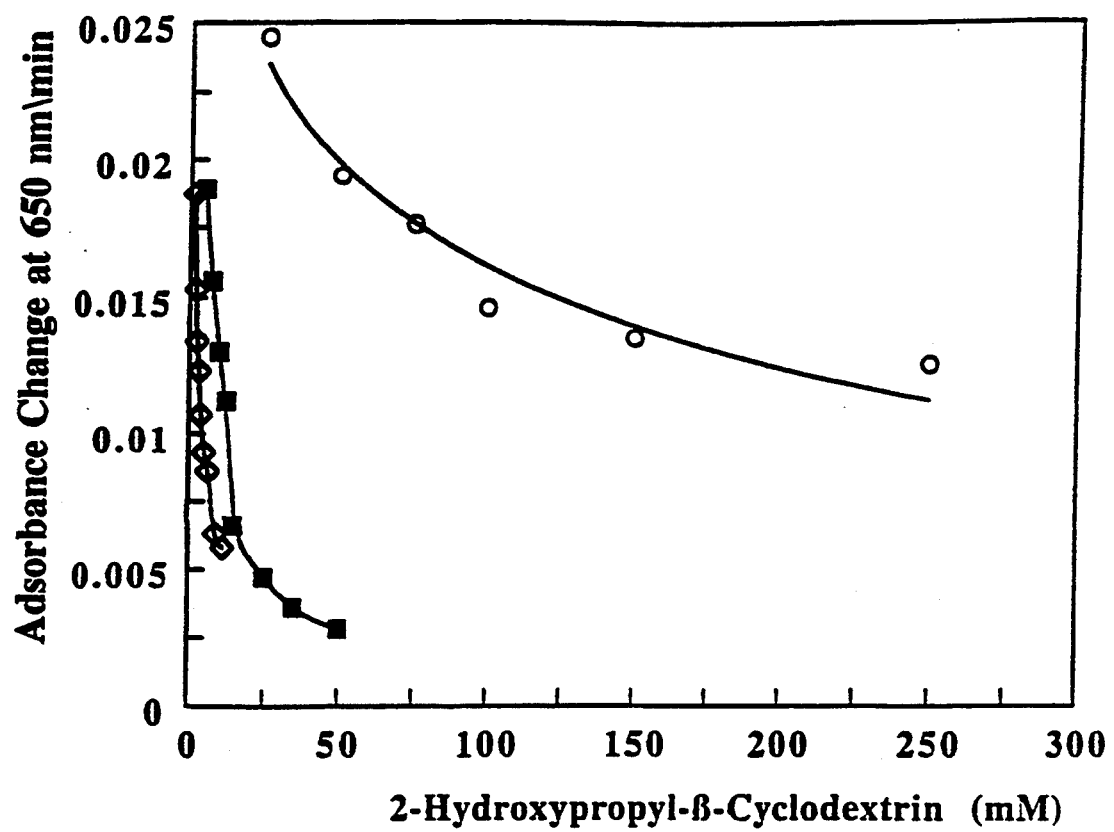

FIG. 8 illustrates the effect of hp-β-CD concentration on the rate of oxidation of 1,1'-dimethylferrocene (DMFeCp$_2$) by bilirubin oxidase (0.005 IU):

○—7.5 mM DMFeCp$_2$.

■—1.5 mM DMFe Cp$_2$;

◇—0.45 mM DMFeCp$_2$

Figure 9:
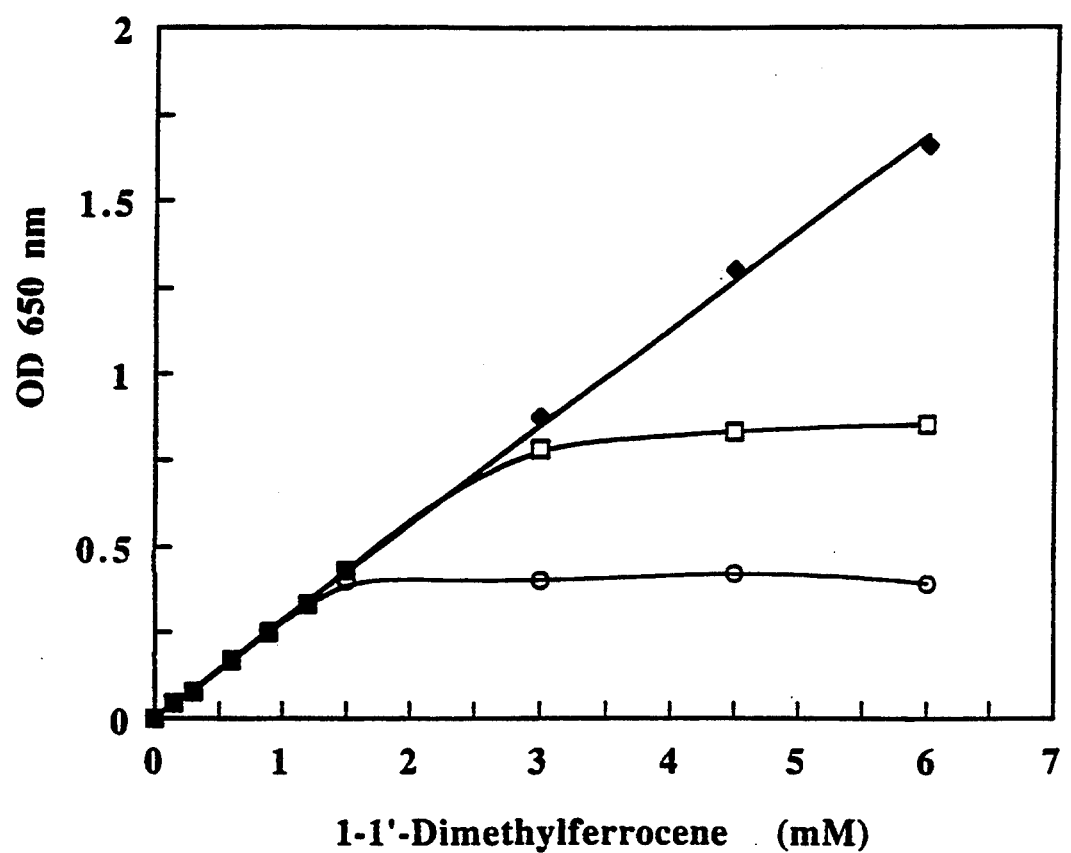

FIG. 9 illustrates the oxygen effect on enzymatic oxidation of 1,1'-dimethylferrocene by bilirubin oxidase:

○—ambient oxygen in buffer;

□—a single pass of oxygen in buffer;

♦—continuous oxygen bubbling.

Figure 10:
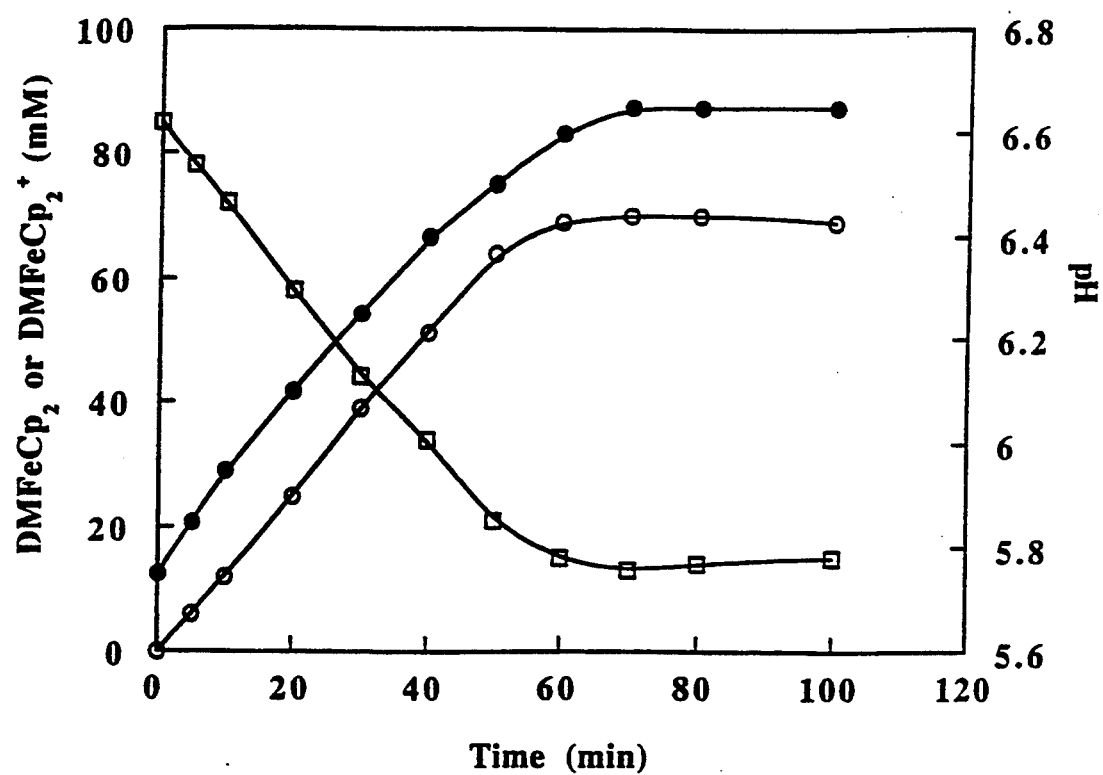

FIG. 10 illustrates the oxidation of 1,1'-dimethylferrocene (DMFeCp$_2$) to 1,1'-dimethylferricinium (DMFeCp$_2$+) by bilirubin oxidase immobilized on aminopropyl glass beads:

□—DMFeCp$_2$;

○—DMFeCp$_2$+;

●—pH.

DETAILED DESCRIPTION OF THE INVENTION

Cyclodextrins (CD), as described for instance in Cyclodextrin Technology, (Topics in Inclusion Science), Jozsef Szejtli, Kluwer Academic Publishers, Dordrecht/Boston/London 1988, Chapter I and II, are cyclic oligosaccharides consisting of 6, 7, or 8 glucopyranose units, usually referred to as α-, β-, or γ-cyclodextrins, respectively. These naturally occurring compounds have relatively rigid doughnut-shaped structures, and have attracted interest as possible natural complexing agents.

The unique structures of these compounds owe their stability to intramolecular hydrogen bonding between the C2- and C3-hydroxyl groups of neighboring glucopyranose units. The molecule takes on the shape of a torus with the C2- and C3-hydroxyls located around the larger opening and the more reactive C6-hydroxyls aligned around the smaller opening. The arrangement of C6-hydroxyls opposite the hydrogen bonded C2- and C3-hydroxyls forces the oxygen bonds into close proximity within the cavity, leading to an electron rich, hydrophobic interior.

The solubility of natural β-cyclodextrin is very poor. Chemical substitutions at the 2,3, and 6 hydroxyl sites greatly increase solubility. Most chemically modified cyclodextrins are able to achieve a 50% w/v concentration in water.

Molecules, or functional groups of molecules which are less hydrophilic than water, can be included in the cyclodextrin cavity in the presence of water, if their molecular dimensions correspond to those of the cyclodextrin cavity. In aqueous solution, the slightly apolar cyclodextrin cavity is occupied by water molecules, an energetically unfavorable process (polar-apolar interaction). These water molecules are therefore readily substituted by appropriate "guest molecules" which are less polar than water. CD is the "host" molecule, and the driving force for complex formation is the substitution of the high-enthalpy water molecules by an appropriate "guest" molecule.

Cavity size is the major determinant of which cyclodextrin is used in complexation. "Fit" is critical to achieving good incorporation into cyclodextrins. Six-glucopyranose unit compounds, α-cyclodextrins, have small cavities which are incapable of accepting many molecules. Eight-glucopyranose unit compounds or γ-cyclodextrins have much larger cavities and hydrophobic functionalities cannot effectively interact to facilitate complexation. The cavity diameter of β-cyclodextrins or 7-glucopyranose unit compounds is well suited for use with molecules the size of hormones, vitamins and many compounds frequently used in tissue and cell culture applications. For this reason, β-cyclodextrin is most commonly used as a complexing agent.

The main molecular dimensions of the respective cyclodextrins are as shown below:

|  | Outside diameter, Å | Inside diameter Å |
|---|---|---|
| α-CD | 14.6 | 4.9 |
| β-CD | 15.4 | 6.2 |
| γ-CD | 17.5 | 7.9 |

For comparison, the interatomic distances of ferrocene and its derivatives are shown below:

| Compound | M—C (Å) | C—C (Å) | Other Distances (Å) | |
|---|---|---|---|---|
| Ferrocene | 2.045 | 1.403 | Inter-ring | 3.32 |
| Ferrocene[a] | 2.03 | 1.43 | Inter-ring | 3.25 |
| Ferrocene[a] | 2.07 | 1.42 | C—H | 1.12 |
| 1,1'-dibenzoyl- ferrocene | 2.05 | 1.41 | C—C (Ph) | 1.39 |
| | | | C=O | 1.21 |
| Ferrocene-1,1' disulfonyl chloride | 1.99 | 1.38 | S—O | 1.55 |
| | | | S—Cl | 2.06 |
| | | | S—C | 1.64 |
| 1,1'(Tetra- methylethylene)- ferrocene | 1.97 (min) 2.11 (max) | 1.45 | angle between ring planes 23° | |
| α-Keto-1,1'- trimethylene ferrocene | 2.008 (min) 2.072 (max) | 1.428 | angle between ring planes, 9.8° | |

[a]by electron diffraction

It can be seen that ferrocene and most of its derivatives can form inclusion (host-guest) complexes with at least β-cyclodextrin. The term "inclusion complex" was introduced in 1950. There are synonyms in the literature, such as adduct, clathrate, molecular compound, cryptate and complex. For the purpose of this specification, the complexing step is referred to as a reaction.

In tests conducted to validate the invention, ferrocene and 1,1'-dimethylferrocene were selected since they possess a relatively low redox potential among known ferrocene-related compounds, as indicated below:

| Ferrocene derivative | $E^o$ (mV)[a] |
|---|---|
| 1,1'-dimethyl | 100 |
| (Ferrocene) | 181 |
| Vinyl | 250 |
| Carboxy | 289 |
| 1,1'-Dicarboxy | 403 |
| (Dimethylamino)methyl | 386 |

EXPERIMENTAL PROCEDURES

Glucose oxidase type X-S (from *Aspergillus niger*), lactate oxidase (from Pediococcus), xanthine oxidase grade III (from buttermilk), L-amino acid oxidase type V (from *Crotalus adamanteus*), glucose-6-phosphate dehydrogenase type XXIV (from *Leuconostoc mesenteroides*), hexokinase, NADH peroxidase, ATP, NAD, NADH, β-D-glucose, L-glutamic acid, L-lactic acid (hemicalcium salt), L-phenylalanine, xanthine, hypoxanthine, uric acid, L-ascorbic acid, sodium sulfite and allantoin were purchased from Sigma (St. Louis, Mo.). Lyophilized pronase and L-glutamate oxidase were obtained from Boehringer Mannheim (Germany) and Yamasa Shoyu Ltd (Choshi, Chiba, Japan), respectively. Alpha cyclodextrin (α-CD), hp-β-CD, and ferrocene were purchased from Aldrich (Milwaukee, Wis.). 1,1'-Dimethylferrocene was obtained from Polysciences (Warrington, Pa.).

Dissolution of Ferrocene and 1,1'-Dimethylferrocene in hp-β-CD.

Solutions of α-cyclodextrin and hp-β-CD were prepared in 20 mM acetate, pH 5.2 buffer to maximum concentrations of 80 mM and 300 mM, respectively. Ferrocene and 1,1'-dimethylferrocene were solubilized in various concentrations of the two cyclodextrins by constant stirring for 2 h. The concentration at maximum solubility was determined spectrophotometrically (Beckman DU-7) using an absorption coefficient of 100 $cm^{-1}M^{-1}$ for both ferrocene and 1,1'-dimethylferrocene at 440 nm and 435 nm, respectively.

Preparation of Ferricinium and 1,1'-Dimethylferricinium.

Solutions (25 mL) of ferrocene (ca. 80 mM) or 1,1'-dimethylferrocene (ca. 90 mM) solubilized in hp-β-CD (250 mM in 100 mM KCl, 100 mM acetate, pH 5.2) were electrochemically oxidized at a platinum foil electrode poised at +450 mV vs an Ag/AgCl reference electrode in a three-electrode system. The counter and working electrodes were separated by a 2M KCl bridge and the electrochemical oxidation was performed using a polarographic analyzer/stripping voltammeter (Princeton Applied Research, Princeton, N.J.). During the course of oxidation, the current was recorded and the absorbencies of ferricinium and 1,1'-dimethylferricinium formed were monitored at 620 nm and 650 nm, respectively. The absorption coefficients for these two cations were determined by adding limiting known concentrations of reducing agents such as ascorbic acid or uric acid. From these values the final concentration of the two ferricinium species could be calculated as well as the percentage conversion for the electrochemical oxidation from the starting solutions.

DETERMINATION OF METABOLITE 1,1'-Dimethylferricinium (ca. 6–8 mM, diluted tenfold from the stock solution), was used with various oxidase enzymes to determine the concentration of their corresponding metabolites in a final assay volume of 500 μL. All metabolite stock solutions were verified by conventional enzyme assy techniques before utilization with the mediator dye. The removal of oxygen by the addition of sulfite or nitrogen bubbling was performed to counteract any possible interferences with the mediator reaction. Oxygen removal was found necessary only for the accurate determination of β-D-glucose in 20 mM acetate buffer, pH 5.2 by glucose oxidase (100 U, 60 min) and glutamate in 150 mM phosphate buffer, pH 7.8 by glutamate oxidase (0.5 U, 30 min). Lactate in 100 mM maleate buffer, pH 9.0 were determined in conjunction with the mediator dye using lactate oxidase (1.0 U, 10 min) and amino acid oxidase (0.31 U, 60 min), respectively. Xanthine and hypoxanthine in 25 mM borate buffer, pH 9.0 were monitored by the reaction with xanthine oxidase (0.18 U, 30 min) and the mediator dye. In this particular case the influence of pH was important to consider. Calibration plots for all metabolites were generated by following the absorbance decrease at 650 nm as the mediator dye was being reduced.

In all cases with real samples, the mediator concentration used was 6–7 mM and the assay volume was 500 μL. β-D-glucose was analyzed from freshly squeezed orange and lemon juice, Welch's grape juice and urine. The μ-D-glucose values obtained were compared to the standard assay procedure (pH 7.8,150 mM $PO_4$) using hexokinase and glucose-6-phosphate dehydrogenase in the presence of ATP, NAD and $MgCl_2$. It should be noted that this assay measures the total D-glucose of which 64% is β-D-glucose. Glutamate was monitored from human blood plasma (Sigma), onion soup mix, and soya sauce (Wong Wing Foods Inc.). The soup mix was dissolved in buffer and then centrifuged, whereas the glutamate in the blood plasma (5 mL equivalent) was first extracted with 5 mL of 10% trichloroacetic acid, then following centrifugation the supernatant was neutralized before being used. The values obtained were compared to the enzyme assay coupling glutamate oxidase and NADH peroxidase. The $H_2O_2$ produced reacted with NADH and the absorbance decrease at 340 nm was monitored. Lactate was monitored from yogurt (Delisle), sour cream (Liberty), buttermilk (Sealtest) and human blood plasma. The yogurt and sour cream (5 g each) were homogenized with buffer (10 mL), centrifuged and the supernatants were used. The comparison was performed by linking lactate oxidase with NADH peroxidase. Aspartame in diet soft drinks such as Sprite, Coke, 7-UP, and Minute Maid orange was completely cleaved after 2 hours reaction with pronase (5.0 mg/ml) in 100 mM maleate buffer, pH 6.5. The phenylalanine released was monitored after a two-fold dilution in 25 mM borate buffer, pH 9. Hypoxanthine from rainbow trout fillets was extracted (3.3 g) in 10% trichloroacetic acid (10 mL) followed by centrifugation and neutralization of the supernatant. Nucleotide degradation in the fillet was allowed to proceed at 4° C. and 25° C. respectively, resulting in higher hypoxanthine levels. The values obtained were verified by monitoring uric acid at 290 nm (absorption coefficient=12,600 $cm^{-1}M^{-1}$) produced from hypoxanthine in the presence of xanthine oxidase.

Determination of Oxidase Activity

The enzyme activities were verified under the conditions specified by the suppliers. The substrate concentration used for each enzyme was at the saturation level with respect to the dye: $\beta$-D-glucose (300 mM), L-glutamate (15 mM), lactate (2.5 mM), L-phenylalanine (2.0 mM), and xanthine/hypoxanthine (2.0 mM). The change in absorbance at 650 nm vs time was plotted against the units of enzyme added.

Characterization of $FeCp_2$ and $DMFeCp_2$ Complexes with Cyclodextrins.

Both $FeCp_2$ and $DMFeCp_2$ were dissolved in methanol or chloroform and exhibited an absorption coefficient of 100 $cm^{-1}M^{-1}$ at 440 nm and 435 nm, respectively. Such a value was then used to estimate the solubility of $FeCp_2$ in cyclodextrin. $FeCp_2$ and $DMFeCp_2$ were only slightly soluble in aqueous solutions (<0.2 mM), but their solubilities were greatly increased by the formation of inclusion complexes with the water-soluble $\alpha$-CD or hp-$\beta$-CD. If a known limiting concentration of either $FeCp_2$ or $DMFeCp_2$ was solubilized in hp-$\beta$-CD (167 mM), the absorption coefficient obtained was still 100 $cm^{1-}M^{-1}$. Hp-$\beta$-CD exhibits a higher solubility (50% w/v) than the $\alpha$-CD D (12–16% w/v) and as a result 300 mM and 80 mM stocks could be prepared, respectively. The inclusion of either $FeCp_2$ or $DMFeCp_2$ by $\alpha$-CD was not very effective since their addition into $\alpha$-CD solutions reduced the solubility of the complexing agent and caused precipitation. The maximum solubility of $FeCp_2$ and $DMFeCP_2$ was about 3–4 mM before precipitation occurred, regardless of the concentration of the $\alpha$-CD tested (26–80 mM). $\beta$-CD and $\gamma$-CD were not tested since the former exhibits a very low solubility in aqueous solutions (1.8% w/v) while the latter is very expensive.

Figure 1:
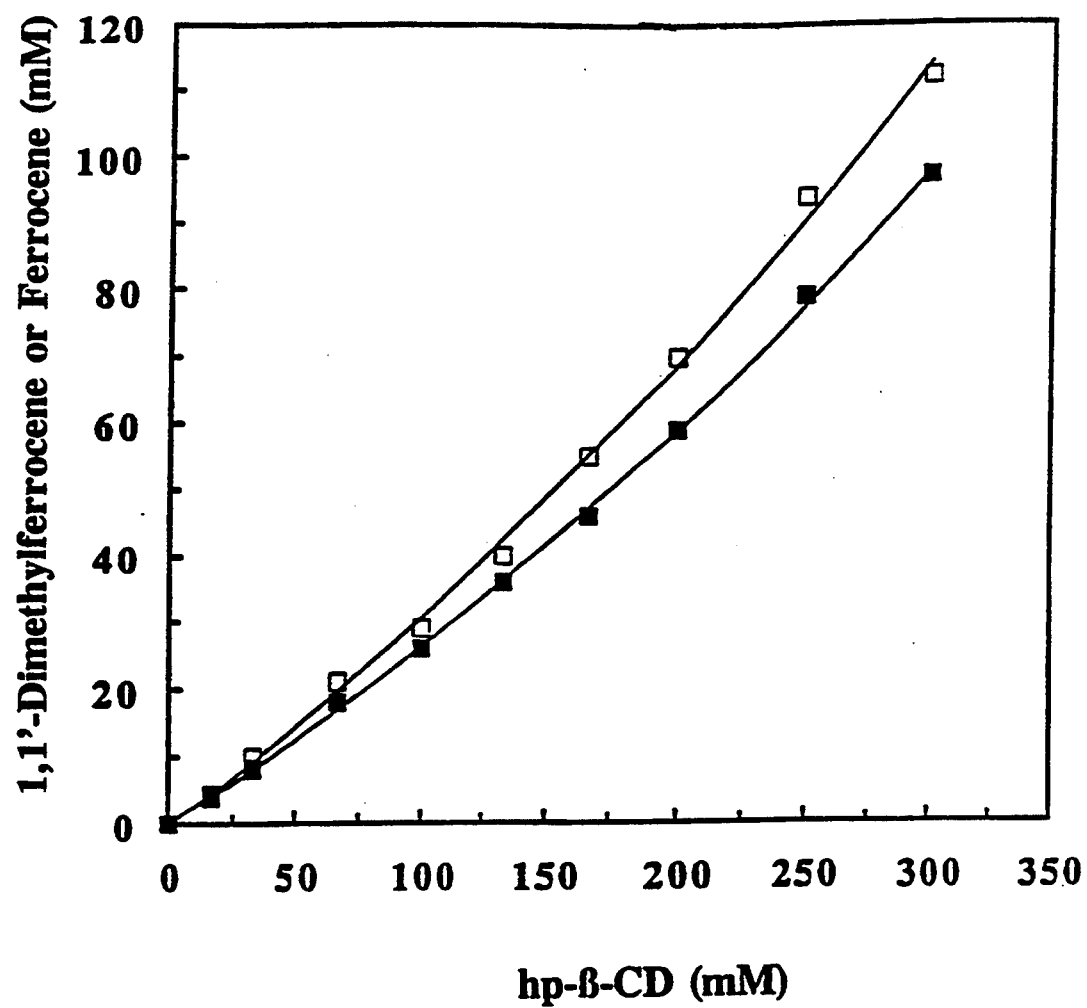
FIG. 1 is a graph illustrating the relationship between the dissolution of ferrocene (FeCp$_2$) and 1,1'-dimethylferrocene (DMFeCp$_2$) and the concentration of hp-β-CD in 20 mM acetate buffer, pH 5.2. 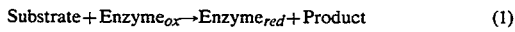—DMFeCp$_2$, 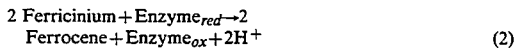—FeCp$_2$.

$FeCp_2$ and $DMFeCp_2$ were both readily soluble in hp-$\beta$-CD. The increased solubility was likely due to the larger cavity (7.8 Å in depth) of the complexing agent when compared to the $\alpha$-cyclodextrin cavity (4.7 Å–6.0 Å). As shown in FIG. 1 the molar ratio of hp-$\beta$-CD to $FeCp_2$ in $FeCp_2$ saturated solutions was 4.2 at the lowest concentration of hp-$\beta$-CD and the ratio decreased slowly to 3.1 at the highest concentration. Similarly, the molar ratio of hp-$\beta$-CD to $DMFeCp_2$ was 3.7 at the lowest concentration and 2.7 at the highest concentration. Therefore it was possible to prepare solutions of $FeCp_2$ or $DMFeCp_2$ as high as 100 mM.

Electrochemical Preparation of $FeCp_2^+$ and $DMFeCp_2^+$.

Figure 2A:
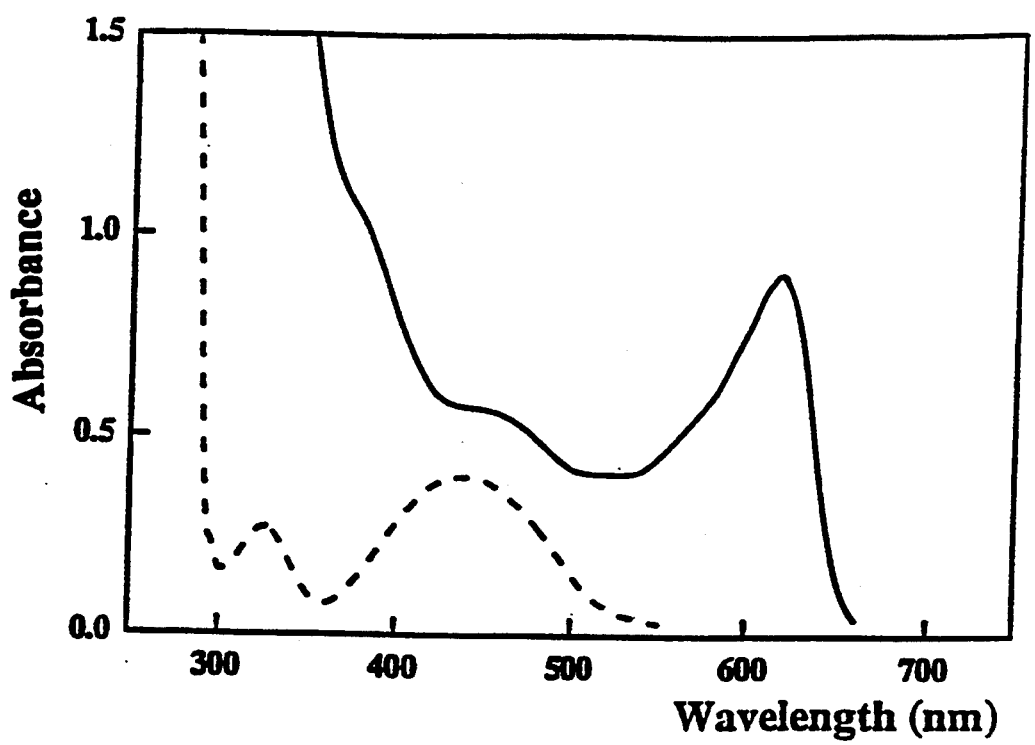
FIGS. 2A and 2B illustrate spectra of ferricinium dyes in 100 mM acetate, 100mMKCl buffer, pH 5.2, as follows.
Figure 2B:
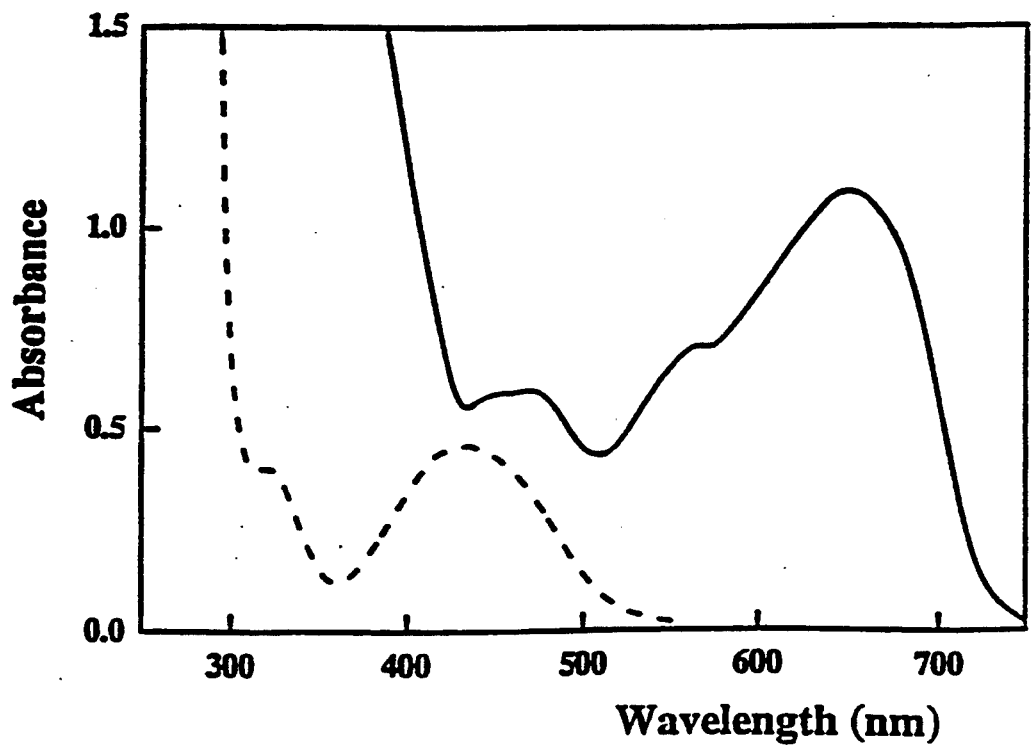

During the time course of oxidation, the current decreased and the solution turned from yellow to green and finally to dark blue. The development of the blue color was monitored at the absorption maximum for $FeCp_2^+$ at 620 nm or $DMFeCp_2^+$ at 650 nM (FIG. 2 A, B). After about 12–16 h, the absorbance reached a plateau while the current continued to decrease For the preparation of $FeCp_2^+$, if the reaction was allowed to proceed further, an absorbance decrease was then noted, indicating the breakdown of the oxidized product. The $DMFeCp_2$ was more stable and did not show the same phenomenon until another 6–8 h had passed. The $FeCp_2^+$ preparation, if terminated in time, still began to degrade after 2–3 days if left in the concentrated form although it was more stable in diluted form (4 months). On the contrary, the concentrated $DMFeCp_2^+$ was stable for at least 4 months when stored at 4° C. This makes the dimethylferrocene the preferred substrate for the purpose of the invention.

It was also noted that the $DMFeCp_2$-hp-$\beta$-CD complex stored at room temperature began to turn green, indicating a preference toward the oxidized state. As also reported, 15 the redox potential of $DMFeCp_2$ is lowest (100 mV) among several known ferrocene-related compounds and this may contribute to the stability of $DMFeCp_2^+$ in comparison to $FeCp_2^+$. Both forms of ferricinium were insensitive to pH variation from 2–11. This characteristic is of advantage since the assay can be performed regardless of some fluctuation in pH and is applicable for a variety of oxidases with different pH optima. Due to the instability of the concentrated $FeCp_2^+$, further studies focused on the electrochemically produced $DMFeCp_2^+$.

Chemical Oxidation of $FeCp_2^+$ and $DMFeCp_2^+$ by Ceric Sulfate or Iodine/KI

Both $FeCp_2$ and $DMFeCp_2$ were oxidized by ceric sulfate or iodine/KI to $FeCp_2H^+$, (ferrocenonium) and $DMFeCp_2H^+$ (1,1'-dimethylferrocenonium), respectively. The reaction was almost instantaneous and the spectra of these two cation species were identical to those of ferricinium and 1,1'-dimethylferricinium. However, the resulting products were not stable against changes in pH and often precipitation occurred with time. Such results were not completely unexpected since in strong acid media ferrocene was reported to undergo extensive protonation on the metal atom.

Enzymatic Oxidation with Bilirubin Oxidase.

Bilirubin oxidase, a commercially available copper-containing enzyme isolated from *Myrothecium verrucaria*, was unexpectedly found to oxidize a yellow 1,1'-dimethylferrocene-2-hydroxypropyl-$\beta$-cyclodextrin complex to a stable blue dye, 1,1'-dimethylferricinium at pH 5–7. So far, bilirubin oxidase has only been reported to oxidize bilirubin, a tetrapyrrole, to produce biliverdin and hydrogen peroxide. During the oxidation process, there was a noticeable increase in pH as a result of the consumption of both $H^+$ and oxygen and the molar ratio between 1,1'-dimethylferrocene and oxygen was established as 4:1. The enzyme was covalently immobilized onto either aminopropyl or arylamine glass beads to form an immobilized enzyme reactor which could be used for the repeated preparation of the blue dye. For bilirubin oxidase immobilized onto the aminopropyl beads, the reaction was much more efficient and completed within 60–90 min corresponding to a conversion yield of 84%. The blue dye was reduced instantaneously by ascorbic acid or uric acid to its original form and its spectrum was insensitive to a wide pH variation from 2 to 11. Application of the blue dye as a colorimetric assay reagent for glucose using glucose oxidase, hypoxanthine using xanthine oxidase, and lactate using lactate oxidase was successfully demonstrated and is described herein. Kinetic studies revealed that the Michaelis-Menten constant for the blue dye with respect to glucose oxidase was noticeably higher than that of lactate oxidase or xanthine oxidase. Details of the laboratory procedures are given below.

Materials:

Bilirubin oxidase (EC 1.3.3.5, from *Myrothecium verrucaria*), glutaraldehyde, aminopropyl (pore size 70 nm, 80–120 mesh) and arylamine (pore size 7.5–10 nm, 200–400 mesh) glass beads were purchased from Sigma (St. Louis, Mo.). Xanthine oxidase (EC 1.1.3.22) was obtained from Boehringer Mannheim (Germany).

Dissolution of 1,1′-dimethylferrocene in hp-β-CD:

Solutions of hp-β-CD were prepared in 200 mM phosphate buffer (pH 6.5) to a concentration of 250mM. $DMFeCp_2$ added in excess was solubilized in hp-β-CD by constant stirring for 3 h at room temperature, followed by centrifugation to remove the remaining undissolved materials. The concentration at maximum solubility was determined spectrophotometrically (Beckman DU 640) using the absorption coefficient of 100 $cm^{-1}M^{-1}$ for $DMFeCp_2$ at 435 nm.

Preparation of 1,1′-dimethylferricinium by soluble enzyme:

Initial experiments were conducted by diluting the $DMFeCp_2$ stock solution (ca. 85 mM) in phosphate buffer to a final concentration of 0.75 mM. The enzymatic oxidation of $DMFeCp_2$ to 1,1′-dimethylferricinium by bilirubin oxidase (0.005 unit) was monitored at 650 nm. The effect of the concentration of phosphate, hp-β-CD, oxygen, bilirubin oxidase and the pH on the rate of enzymatic oxidation was investigated. The Michaelis constant $K_m$ of $DMFeCp_2$ was also calculated at fixed concentrations of hp-β-CD.

A stock solution of $DMFeCp_2$ (40 ml, 85 mM, in 200 mM phosphate, 250mM hp-β-CD pH 5.8) was then oxidized using 6.5 units of the soluble bilirubin oxidase. Pure oxygen was continuously bubbled to the reaction (0.09 l/min) and the formation of the blue dye was monitored spectrophotometrically at 650 nm. After completion of the reaction the enzyme was destroyed by lowering the pH to 2.5 since bilirubin oxidase was denatured at this acidic condition.

Immobilization of bilirubin oxidase:

The aminopropyl glass beads (500 mg) were washed with phosphate buffer saline PBS (9 g/l sodium chloride, 20 mM phosphate, pH 7) and then activated by reacting with glutaraldehyde (3 ml, 2.5% w/v) in PBS for 2–3 h at room temperature (20°–24° C.). The orangish-pink beads were washed extensively to remove excess glutaraldehyde. Bilirubin oxidase solution (50 units, 1.6 mg protein) in 20 mM phosphate (pH 7) was mixed with the activated glass beads in a capped tube and slowly rotated overnight at 4° C. The resulting beads were rinsed with 200 mM phosphate (pH 6.5) to remove unbound enzyme, and stored at 4° C.

The arylamine glass beads (500 mg) were washed with PBS followed by a 1M HCl solution. The beads in 20 ml of 1M HCl were activated to the diazo form by the slow addition of 20 ml of 0.5M sodium nitrite solution at 0°–4° C. for 45 min. The beads were rinsed with cold 0.1M HCl followed by 0.2M sodium bicarbonate (pH 8). The resulting reddish-brown beads were mixed with the bilirubin oxidase solution (as above) overnight at 4° C. After rinsing with 200 mM phosphate (pH 6.5) the immobilized enzyme beads were stored at 4° C. Detailed information of these two immobilization procedures can be found in Male et al, Appl. Biochem. Biotechnol. 38, 189–201, 1993.

Determination of metabolites:

1,1′-dimethylferricinium (ca. 6.5–7.5 mM, diluted ten-fold from the stock solution) was used with various oxidases to determine the concentration of their corresponding metabolites in a final volume of 500 μl . Metabolite stock solutions were verified by conventional enzyme assay techniques. Lactate in 100 mM maleate buffer (pH 6.5) and phenylalanine in 100 mM borate buffer (pH 9.0) were determined in conjunction with the dye using lactate oxidase (1 IU, 10 min) and L-amino acid oxidase (0.31 IU, 60 min). Hypoxanthine in 100 mM borate buffer (pH 9.0) or 250 mM acetate buffer (pH 5.2) was monitored by reaction with xanthine oxidase (0.10 IU, 30 min). In this particular case, the influence of pH was important since uric acid, a product of this enzymatic reaction, is reported to reduce $DMFeCp_2^+$ instantaneously at pH above 8; whereas reduction did not occur at pH below 6. β-D-glucose in 250 mM acetate buffer (pH 5.2) was determined using the dye and glucose oxidase (10 IU, 30 min).

Oxidation of $DMFeCp_2$ by soluble bilirubin oxidase

When soluble bilirubin oxidase (0.02 IU) was added to a dilute solution of $DMFeCp_2$ (0.75 mM) the solution turned from yellow to green and finally blue, an indication of 1,1′-dimethylferricinium formation. The development of the blue color was monitored at the absorption maximum for $DMFeCp_2^+$ at 650 nm. The oxidation of $DMFeCp_2$ to $DMFeCp_2^+$ by bilirubin oxidase was not affected by phosphate buffer up to 200 mM. The effect of bilirubin oxidase concentration on the rate of oxidation of $DMFeCp_2$ (1.5 mM) was monitored and a linear relationship was obtained up to 0.02 units, with a slope of 3.8 $OD_{650nm}$/min/unit (5.8 μmol/min/unit). As shown in FIG. 7, bilirubin oxidase exhibited a broad pH optimum (5–7) with respect to $DMFeCp_2$. However, the ability of bilirubin oxidase to oxidize $DMFeCp_2$ was adversely affected at pH above 7.5. It is worth noting 25 that bilirubin oxidase was reported to have a maximum activity at pH 8 with respect to its ability to oxidize bilirubin (tetrapyrrole) to biliverdin and hydrogen peroxide (Murao, S. & Tanaka, N. Agri. Biol. Chem. (1981) 45, 2383–2384).

At fixed concentrations of $DMFeCp_2$, an increase in the concentration of hp-β-CD decreased the rate of oxidation of $DMFeCp_2$ and such an effect became more pronounced at low levels of $DMFeCp_2$ (FIG. 8). As the concentration of hp-β-CD increased from 1.5 to 5 to 25 mM, the $K_m$ for $DMFeCp_2$ also increased from 0.53 to 1.43 to 3.21 mM.

The oxygen effect on the oxidation of $DMFeCp_2$ to $DMFeCp_2^+$ by bilirubin oxidase is clearly illustrated in FIG. 9. Under limiting oxygen, the maximum absorbance increase at 650 nm was only 0.40, corresponding to 1.20 mM $DMFeCp_2^+$ produced. Since the level of ambient dissolved oxygen in aqueous solution is about 0.25–0.35 mM, the molar ratio of the reaction between DMFeCp2 and O2 was estimated to be 4:1. The stoichiometry was confirmed by a single pass of air through the reaction mixture which doubled the value of the absorbance measured (0.8). Bilirubin oxidase is reported to be inactive in the absence of oxygen and the enzyme contains no NAD, NADP, FAD, or FMN. When air was constantly bubbled through the solution, a straight line resulted with a slope of 0.28 OD/mMDMFeCp2, indicating that the conversion of DMFeCp2 to DMFeCp2+ was about 84%. For complete conversion, the slope must be 0.333 OD/mM which reflects the absorption coefficient of the blue dye.

Performing the oxidation of DMFeCp2 (85 mM, 40 ml) to DMFeCp2+ using 6.5 units of bilirubin oxidase with constant oxygen bubbling, the reaction proceeded to 85% completion in about 2 h (3.7 μmol/min/unit) with a concomitant pH increase from 5.7 to 6.7. Such a pH change was not totally unexpected since the oxidation of DMFeCp2 to DMFeCp2+ will consume both oxygen and H+ and the stoichiometry should be similar to that described for the oxidation of iron (II) to iron (III) by ceruloplasmin:

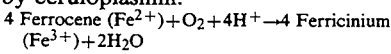

This reaction was validated by the 4:1 molar ratio between DMFeCp2 and O2 obtained earlier and partly by the fact that bilirubin oxidase could not oxidize DMFeCp2 efficiently at alkaline pH conditions.

The final product containing both DMFeCp2+ (85%) and DMFeCp2 (15%) in the presence of the enzyme was not stable after the completion of the reaction. If left for an extra hour at room temperature, about 10% of the blue dye was lost as confirmed by an absorbance decrease at 650 nm. The reason was not understood, however, one may expect that ferricinium could be further oxidized by the enzyme to form $Fe(OH)_3$, particularly under alkaline conditions. The enzyme was destroyed by lowering the pH to 2.5 and after 2 min incubation, the pH was readjusted to 6.8. In this case, the product remained stable for 2 months when stored at 4° C., implying complete enzyme denaturation. It should be noted that the absorption characteristics of the blue dye were not affected by a pH variation from 2.5 to 11.

At this point, it is important to stress that besides bilirubin oxidase, various copper-containing enzymes including ceruloplasmin were tested for their ability to oxidize DMFeCp2. Only bilirubin oxidase and ceruloplasmin exhibited significant oxidation activity toward DMFeCp2 with respect to the conversion yield and the reaction time. However, the former enzyme was selected in view of the cost, its wide pH optimum as well as the capability to be immobilized onto the aminopropyl or arylamine glass beads. An attempt to immobilize ceruloplasmin onto such glass beads was not successful since the resulting beads exhibited a minimal activity compared to that of bilirubin oxidase.

Oxidation of DMFeCp2 by immobilized bilirubin oxidase

Bilirubin oxidase was efficiently immobilized onto either aminopropyl or arylamine glass beads since no bilirubin oxidase activity or protein was detected in the supernatant after overnight stirring with the activated beads. The bilirubin oxidase immobilized onto the aminopropyl glass beads was then used to oxidize DMFeCp2 to DMFeCp2+. As shown in FIG. 10, the oxidation was completed in 60–90 min, during which time the pH increased from 5.7 to 6.7 due to the release of OH− (or H+ consumption) as described previously.

The conversion yield was determined to be 84±2% (n=7) and since the residual amount of DMFeCp2 was 15% there was no loss of starting material, and equilibrium was reached. Over the course of one week, the beads were used to oxidize DMFeCp2(85 mM, 40 ml) seven times without any noticeable decrease in the efficiency. In these experiments, about 84% conversion yield was always achieved in 60–90 min. By comparison, the electrochemical oxidation of DMFeCp2 to DMFeCp2+ was found to require 12–16 hours and the rate of conversion was only 76%

Bilirubin oxidase immobilized on arylamine beads also oxidized DMFeCp2 to DMFeCp2+ with a conversion yield of 84%. Similarly, the pH increased from 5.7 to 6.7 and the arylamine beads were also able to oxidize DMFeCp2 to DMFeCp2+ seven times without any decrease in their efficiency. However, the reaction time was noticeably longer at 3–4 h. In view of the capacity for the oxidation of DMFeCp2, bilirubin oxidase immobilized on arylamine beads was much less efficient. However, it is worth noting that bilirubin oxidase was immobilized onto the aminopropyl glass beads via the amino groups whereas, in the case of arylamine beads, the azo linkage was formed via the tyrosine groups of the enzyme. The slower response with the arylamine beads may imply that the tyrosine groups are close to the binding sites of the bilirubin oxidase for DMFeCp2.

Besides DMFeCp2, soluble bilirubin oxidase would also oxidize ferrocene (FeCp2) to ferricinium, but the oxidation of the substrate was much less efficient. At low concentrations of ferrocene, the conversion yield was estimated to be 85% using the absorption coefficient for FeCp2+ at 620 nm (425 cm−1M−1). However, at a high ferrocene concentration (85 mM), the conversion yield was only 38%, but surprisingly the product was stable for 2 months when stored at 4° C. As indicated hereinabove, concentrated ferricinium prepared by electrochemical oxidation was stable for only 2 days.

Characteristics of DMFeCp2+ produced by immobilized bilirubin oxidase

Similarly to the DMFeCp2+ produced electrochemically, the absorption characteristics of dimethylferricinium produced by immobilized bilirubin oxidase were insensitive to pH variation from 2 to 11. This is advantageous since assays can be performed for a variety of oxidases with different pH optima. The dye in the concentrated form was stable upon storage at 4° C. for at least 2 months without any loss of its absorbency. As well, the dye exhibited a calibration linearity up to 9 mM ($OD_{650nm}$=3.0) when using plastic cuvettes (1 cm Sarstadt).

Effect of Reducing Agents on the DMFeCp2+.

Figure 3:
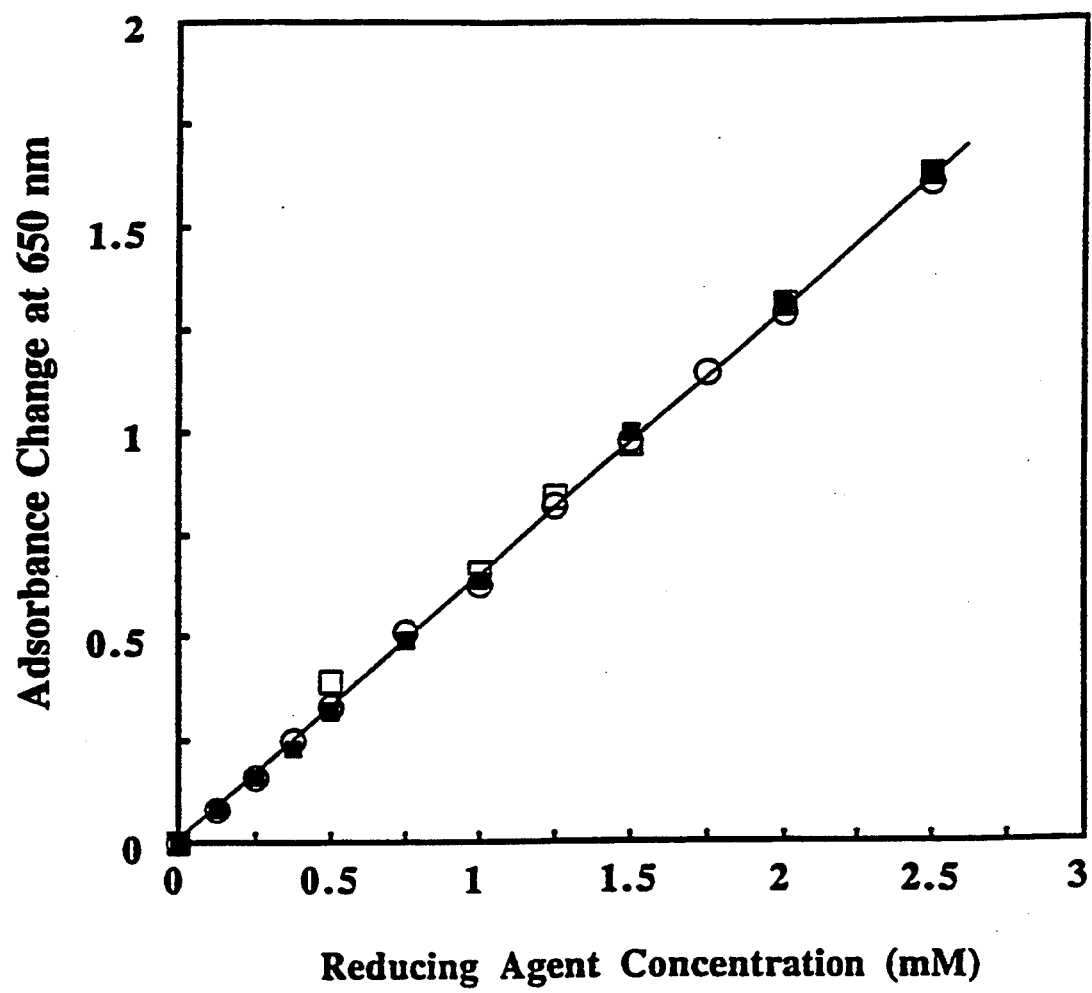
FIG. 3 illustrates the effect of reducing agents on DMFeCp$_2$+ (slope is determined at 95% confidence interval)

Ascorbic acid reduced the dye instantly over a wide pH range of 5–9. Uric acid only reduced the DMFeCp2+ rapidly at alkaline pH (>8). At neutral pH, the rate of reduction was very slow and below pH 6, uric acid exhibited no reducing capability. Similarly, sulfite was able to reduce the dye rapidly at pH above 8. However, at pH 7 and 5.2, the slower rate of reduction of the dye should be taken into account if sulfite is used for oxygen removal as discussed later. As shown in FIG. 3, the average slope of the three lines at 95% confidence interval (0.653±0.017 $OD_{650nm}$/mM) results in an absorption coefficient of 326±8.5 cm−1M−1 for the DMFeCp2+. From the absorption coefficient obtained, the concentration of the stock DMFeCp2+ was determined to be 68 mM, corresponding to 76% conversion of the starting DMFeCp$_2$/hp-$\beta$-CD complex. In comparison, the conversion of FeCp$_2$ to FeCp$_2^+$ was 56% with a final concentration of 45 mM ferricinium. The absorption coefficient obtained for FeCp$_2^+$ was 425 cm$^{-1}$M$^{-1}$ which agreed favorably with the value reported by other workers. Response of DMFeCp$_2^+$ to Various Metabolites.

DMFeCp$_2^+$ had a calibration linearity up to 9 mM (OD$_{650}$=3.0) when using plastic cuvettes (1 cm Sarstedt). However, the linearity was limited to about 5 mM (OD$_{650}$=1.7) with other cuvettes such as quartz or glass. The DMFeCp$_2^+$ dye was investigated with various concentrations of glucose and the reduction was initiated by adding glucose oxidase. The response to glucose was nonlinear rather than a straight line with the anticipated slope of 0.65 OD/mM. Such a result would not be totally unexpected since there was a competition for the reduced enzyme between the DMFeCp$_2^+$ mediator and oxygen (FIG. 4). Oxygen (normally 0.2–0.3 nM) in the buffer or glucose containing samples, could be removed by nitrogen bubbling or by adding excess sodium sulfite (0.4 mM) for 5–10 min. Since the glucose oxidase reaction was carried out at pH 5.2, when sulfite was added to remove oxygen 10 min was allowed for a complete reaction between the residual sulfite and the dye (50 μL) before enzyme was added. As expected, the reduction of the dye before enzyme addition was equivalent to 0.1–0.2 mM and the removal of oxygen by either nitrogen bubbling or the sulfite method resulted in a straight line for glucose calibration with a slope of 0.671 OD/mM (FIG. 4).

Similar to glucose measurement, for the assay of glutamate by glutamate oxidase, the removal of oxygen was necessary to generate a linear relationship. The residual sulfite was expected to react instantly with the dye since the assay was performed at pH 7.8. The slope of the calibration was 0.649±0.019 OD/mM (figure not shown, 95% confidence interval, n=10, R$^2$=0.998) Although in both cases the mediator concentration was in excess compared to oxygen (6.8 mM vs 0.2–0.3 mM) the competition could still arise if the K$_m$ of the oxygen for the reactions is much lower than that of the mediator. Using lactate oxidase and amino acid oxidase, lactate and phenylalanine monitored with DMFeCp$_2^+$ resulted in slopes of 0.663±0.003 and 0.652⊔0.005 OD/mM (95% confidence interval, n=10, R$_2$=0.999 for both), respectively. In both cases the removal of oxygen did not alter the results indicating that there was no competition between oxygen and the mediator dye for the reduced enzyme concerned. For xanthine and hypoxanthine the reaction was first conducted at pH 5.2. There are two oxidation steps from hypoxanthine to uric acid in the presence of xanthine oxidase and only one oxidation step from xanthine to uric acid. It should be noted that each reduced enzyme will require two ferricinium ions.

As expected, the results indicated two reducing equivalents (slope=0.658 OD/mM) for xanthine and four reducing equivalents (slope=1.323 OD/mM) for hypoxanthine (FIG. 5) since the uric acid produced could not reduce the DMFeCp$_2^+$ at this pH. However, when the pH was raised to 9 the results of FIG. 5 indicated six reducing equivalents for xanthine (slope=1.95 OD/mM) and eight reducing equivalents for hypoxanthine (slope=2.555 OD/mM). Results indicated that at this pH, the uric acid produced from the xanthine oxidase was further oxidized by the crude enzyme source and reduced the DMFeCp$_2^+$ by four reducing equivalents. Where uric acid was allowed first to react completely with the DMFeCp$_2^+$ before adding xanthine oxidase, no further reduction of the mediator was noted (only two reducing equivalents). Adding uric acid and the enzyme simultaneously resulted in four reducing equivalents which implies that the oxidation process for uric acid was somewhat different in the two cases. It was thought that allantoin, one of the known products of uric acid oxidation, may interact with the dye to produce two reducing equivalents. Experimental data, however, revealed that at this pH the DMFeCp$_2^+$ dye did not react with allantoin alone or a mixture of enzyme and allantoin. Due to these additional reducing equivalents the sensitivity of the dye system for detecting hypoxanthine was four-fold greater than any of the other metabolites tested.

Measurement of Metabolites in Samples

The new DMFeCp$_2^+$ dye accurately estimated the values of all five metabolite tested in real samples and the results compared favorably with the conventional enzyme assay techniques (Table 1). The average error determined at 95% confidence interval was 4.89±1.97%.

Urinary glucose could be measured at pH 5.2, since the large contaminating levels of uric acid had no interfering effects at this pH. Before the addition of glucose oxidase, the dye was reduced more than the level expected from the excess sulfite used for oxygen removal. This could have been caused by ascorbic acid, which can reach levels as high as 0.2 mM, or some other reducing agents in the urine. However, the level of interference at pH 5.2 was quite low indicating that urine could be examined using DMFeCp$_2^+$ for other metabolites which could be linked to oxidase enzymes. When the assay was attempted at pH 7.8 the dye was completely reduced due to the presence of uric acid which can reach levels from 4–10 mM. Good correlation without interference was also observed between the dye technique and the reference hexokinase procedure for glucose levels in food products.

Glutamate was measured accurately in food samples as well as human blood plasma. Before addition of the glutamate oxidase there was no significant interference noticed at pH 7.8 between the blood plasma and the DMFeCp$_2^+$. This leads to the possibility of monitoring other metabolites in the blood such as glucose, lactate and pyruvate which can be linked to oxidases and mediated by DMFeCp$_2^+$. The present high cost of glutamate oxidase makes the assay of glutamate using the dye less attractive.

Lactate, an important index of freshness and hygienic quality, was determined very precisely in a variety of dairy products. A yogurt sample was monitored over one week and as expected the level of lactate had increased. The human blood plasma sample tested had a lactate level of 1.4 mM, close to the normal resting levels of lactate found in venous blood (0.5–1.3 mM). High levels of lactate in the blood have been associated with many pathological symptoms such as heart disease, diabetes, coma, asphyxia, and pneumonia. Among several enzymes tested, lactate oxidase appeared to be one of the most promising candidates to use with DMFeCp$_2^+$. The enzyme amount required was low (1 unit), the assay time was fast (10 min) and the oxygen removal was not required.

Aspartame levels were measured accurately in diet soft drinks as an example for phenylalanine measurement using amino acid oxidase. Aspartame samples are very low in contaminating amino acids so that no interferences were noticed even though amino acid oxidase is not a very specific enzyme. The level of hypoxanthine in fish tissue was precisely monitored using the $DMFeCp_2^+$. As expected, the level of hypoxanthine, an indicator of fish freshness, increased as time progressed at 4° C. and the degradation was much faster at room temperature.

Determination of Oxidase Activities

The five enzymes monitored at saturating concentrations of their substrates resulted in linear relationships between $\Delta OD_{650}$/min and number of enzyme units. Oxygen was not removed by sulfite in the assays for glucose and glutamate as no increase in rate was observed. The slope of the lines in $\Delta OD$/min/unit vary due to the differences in the definition of the unit by the manufacturers for each enzyme. In addition, the assay conditions specified by the manufacturer with respect to pH and temperature are not necessarily the same conditions used for the $DMFeCp_2^+$ assay. Also, the unit definitions of the manufacturers are using oxygen as the co-substrate of the metabolites rather than $DMFeCp_2^+$. However, from the slopes of these lines a correlation could be made between an unknown source of an oxidase being purified and the conventional definition given for the same commercially available enzyme. The slope values obtained for xanthine oxidase with xanthine and hypoxanthine were close to the predicted ratio of 3 to 4 based on the reducing equivalents (FIG. 6). Another alternative would be to define the unit for any particular oxidase activity based simply on the dye assay itself; such that one unit of enzyme activity corresponds to the reduction of 1 μmole of $DMFeCp_2^+$ to $DMFeCp_2$ per min at 25° C.

In brief, the new assay technique has proven to be very useful in monitoring the activity of various oxidases under saturated substrate condition. Therefore, it may serve as a new methodology for screening, isolation the purification of these enzymes. Alternatively, together with oxidases the new dye could be applicable for determination of several important target analytes. Although the absorption coefficient of the new dye is considerably lower than that of the NAD-NADH system, the advantages of this new dye are two-fold: (i) the new dye should be more applicable to various colored samples since the absorbance can be followed at 620–650 nm vs 340 nm for the NAD-NADH system and (ii) it requires no other expensive coupling enzymes and reagents.

It should be appreciated that the present authors are not in a position to define the structure of the (blue) redox dye of the present invention; it is not known whether its relationship to the cyclodextrin "host" is different or identical as in the intermediate inclusion complex. For this reason, the dye is claimed as a "product-by-process".

TABLE 1

| | Metabolite Concentration in Samples Determined by $DMFeCp_2^+$ Dye | | | |
|---|---|---|---|---|
| Metabolite | Sample source | $DMFeCp_2^+$ Assay[1] (mM) | Conventional Enzymatic Assay (mM) | % Difference |
| β-D-Glucose | Orange Juice | 59 (2.3) | 62 (0.58) | −4.84 |
| | Lemon Juice | 16 (1.58) | 18 (0.23) | −11.11 |
| | Welchs Grape Juice | 240 (6.9) | 250 (6.5) | −4 |
| | Urine #1 | 1.3 (0.058) | 1.1 (0.017) | +18.18 |
| | Urine #2 | 0.39 (0.043) | 0.38 (0.032) | +2.63 |
| Glutamate | Soya Sauce | 80 (1.2) | 83 (1.7) | −3.61 |
| | Onion Soup Mix | 34 mg/g (0.58) | 35 mg/g/ (1.2) | −2.86 |
| | Human blood plasma | 0.24 (.012) | 0.27 (0.006) | −11.11 |
| Lactate | Human Blood Plasma | 1.42 (0.046) | 1.49 (0.046) | −4.7 |
| | | 83 (0.58) | 84 (3.5) | −.1.19 |
| | Buttermilk | 84 μmol/g (0.58) | 86 μmol/g (4.6) | −2.32 |
| | Sour cream | 73 μmol/g (0.58) | 74 μmol/g (0.58) | −1.35 |
| | Yogurt #1 | 94 μmol/g (1.2) | 92 μmol/g (1.2) | +2.17 |
| | Yogurt #2 (1 wk later) | | | |
| Phenylalanine | Sprite | 1.72 (0.0073) | 1.67* | +2.994 |
| | Coke | 1.87 (0.046) | 1.77* | +5.65 |
| | 7-Up | 1.69 (0.017) | 1.67* | +1.2 |
| | Minute Maid | 1.85 (0.0058) | 2.04* | −9.31 |
| Hypoxanthine | Trout | 2.2 μmol/g (0.04) | 2.2 μmol/g (0.0006) | 0 |
| | Trout 1d 0° C. | 2.1 μmol/g (0.075) | 2.4 μmol/g (0.13) | −12.5 |
| | Trout 6d 0° C. | 4.8 μmol/g (0.058) | 4.7 μmol/g (0.006) | +2.13 |
| | Trout 13d 0° C. | 5.8 μmol/g (0.15) | 5.6 μmol/g (0.15) | +3.57 |
| | Trout 1d 25° C. | 4.0 μmol/g (0.095) | 3.8 μmol/g (0.12) | +5.26 |
| | Trout 2d 25° C. | 4.5 μmol/g (0.02) | 4.5 μmol/g (0.064) | 0 |
| | | | | Average error (95% confidence interval): 4.89 ± 1.97 |

[1]average of 4 repeated measurements; the value in bracket represents the standard error of the mean (standard deviation over the square root of the sample size)
*specified by the manufacturers

We claim:

1. A process for preparing an intermediate of a redox dye, comprising
   reacting 1,1'-dimethylferrocene with 2-hydroxypropyl-β-cyclodextrin, to obtain a water-soluble inclusion complex.

2. A process for preparing a redox dye, comprising
   oxidizing the inclusion complex of claim 1 thereby converting 1,1'-dimethylferrocene to 1,1'-dimethylferricinium.

3. The process according to claim 2 wherein the oxidizing step is carried out by electrochemical oxidation of the inclusion complex.

4. The process according to claim 2 wherein the oxidizing step is carried out by reacting the inclusion complex with bilirubin oxidase.

5. The process according to claim 4, wherein the bilirubin oxidase is immobilized.

6. The process according to claim 5 wherein the bilirubin oxidase is immobilized on aminopropyl glass beads.

7. An intermediate of a redox dye comprising a water-soluble inclusion complex of 1,1'-dimethylferrocene and 2-hydroxypropyl-$\beta$-cyclodextrin.

8. The redox dye prepared by the process of claim 2.

* * * * *